US00PP25290P2

(12) United States Plant Patent
Kordes

(10) Patent No.: US PP25,290 P2
(45) Date of Patent: Feb. 17, 2015

(54) SHRUB ROSE PLANT NAMED 'KORCONVENT'

(50) Latin Name: *Rosa hybrida*
Varietal Denomination: KORconvent

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 1 day.

(21) Appl. No.: 13/986,313

(22) Filed: Apr. 18, 2013

(51) Int. Cl.
*A01H 5/00* (2006.01)

(52) U.S. Cl.
USPC ..... Plt./105

(58) Field of Classification Search
USPC ..... Plt./104, 105, 135, 146
See application file for complete search history.

(56) References Cited

PUBLICATIONS

HelpMeFind, obtained from http://www.helpmefind.com/rose/pl.php?n=89262 on Jun. 6, 2014.*
South Africa Application for Plant Breeders' Rights (PBR).
South Africa Grant of Plant Breeder's Rights.
Print-out of KORconvent page on HelpMeFind.com (obtained from http://helpmefind.com/gardeninhg/l.php?l-2.67470 on Jun. 27, 2014).
Print-out of KORconvent page on LudwigsRoses.co.za (obtained from http://www.ludwigsroses.co.za/flower/rosafrica/ on Jun. 19, 2014).

* cited by examiner

*Primary Examiner* — June Hwu
*Assistant Examiner* — Keith Robinson

(57) ABSTRACT

A new and distinct variety of rose with long lasting, novel apricot flowers and attractive foliage with above average disease resistance. It exhibits bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORconvent'. The new variety of rose plant of the present invention originated from a controlled crossing in a breeding program of two distinct parents during the summer of 2004. The crossing was between 'KORunrok', a non-patented rose, and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORconvent'.

CROSS REFERENCES AND FEDERAL R&D STATEMENT

There are no cross referenced or related applications. This variety was developed without the aid of any research grant.

SUMMARY OF THE INVENTION

The new rose plant may be distinguished from its seed parent, 'KORunrok', by the following combination of characteristics:

1. The seed parent has cream white flowers while 'KORconvent' has apricot flowers.

2. The seed parent has an upright growth habit while 'KORconvent' has a bushy growth habit.

The new rose plant may be distinguished from its pollen parent, an 'un-named seedling', by the following combination of characteristics:

1. 'KORconvent' has a very double petal count while the pollen parent has a double petal count.
2. 'KORconvent' has a more compact habit than the pollen parent.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORconvent' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORconvent' was selected in May, 2005 from the seedling beds to be asexually propagated for further evaluation. The first asexual propagation of 'KORconvent' was done by budding to seedling understocks in July, 2005 at the inventor's nursery in Offenseth-Sparrieshoop, Germany.

This initial and other subsequent propagations conducted in controlled environments demonstrate that 'KORconvent' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORconvent'.

DETAILED BOTANICAL DESCRIPTION

The following is a description of 'KORconvent', as observed growing in October, 2012 in a nursery in Jackson County, Oreg. on plants of 3 years of age. Color references are made using The Royal Horticultural Society (London, England) Colour Chart, 2001 except where common terms of color are used.

For a comparison, several physical characteristics of the rose variety 'KORlubaja', a rose variety from the same inventor described and illustrated in U.S. Plant Pat. No. 23,667 with an issue date of Jun. 18, 2013, are compared to 'KORconvent' in Chart 1.

CHART 1

| Characteristic | 'KORconvent' | 'KORlubaja' |
|---|---|---|
| Average number of petals | 25-32 | 20-22 |
| Fragrance | Moderate | Little to no fragrance |
| Flower color upon opening, petals; outermost petal; outer side | Orange-White Group 159A | Red Group 53C |

Parents:

*Seed parent*.—'KORunrok'.

*Pollen parent*.—An 'un-named seedling'.

Classification:

*Botanical classification*.—*Rosa hybrida* 'KORconvent'.

*Commercial classification*.—Shrub.

FLOWER AND FLOWER BUD

Blooming habit: Recurrent.

Flower bud:

*Size*.—Upon opening, 35 mm in length from base of receptacle to distal end of bud and 30 mm diameter at its widest point.

*Bud form*.—Long. Pointed ovoid.

*Bud color*.—As sepals first unfold, bud color is Orange Group 27A with middle zone Yellow-Orange Group 23C. When ¼ open, the upper surface of petals is Yellow-Orange Group 23A, and the lower surface is Orange Group 24D. Guard Petals are a combination of Yellow-Orange Group 23C and Orange-Red Group N34C.

*Sepals*.—Color: Upper surface Yellow-Green Group 144B with intonations of Greyed-Red Group 182B. Lower surface Yellow-Green Group 144A with intonations of Greyed-Red Group 182C. Size: Average 28-32 mm (l)×6-10 mm (w). Shape: Weak foliaceous appendages on 2 of the 5 sepals. Apex: Apiculate. Base: Flat at union with receptacle. Quantity: Five. Surface texture: Upper side: Pubescent. Lower surface: Lightly pubescent. Margins: Pubescent with stipitate glands.

Receptacle:

*Surface*.—Smooth glossy.

*Color*.—Yellow-Green Group 144A with intonations of Greyed-Red Group 182B.

*Shape*.—Urn-shaped.

*Size*.—10-12 mm (h)×14-16 mm (w).

Peduncle:

*Surface*.—With abundant stipitate glands.

*Length*.—60 to 80 mm average length.

*Diameter*.—3 to 6 mm average diameter.

*Color*.—Yellow-Green Group 146C with intonations of Greyed-Red Group 182A.

*Strength*.—Average strength.

*Borne*.—Multiple flower buds per stem, generally 3 to 5.

*Type of inflorescence*.—Corymbous.

*Size of inflorescence*.—40 to 50 cm in length.

*Number of flowers per inflorescence*.—5 to 15 flowers on average.

Pedicel:

*Surface*.—Papillate, with abundant stipitate glands present.

*Length*.—45 to 55 mm.

*Color*.—Yellow-Green Group 146C.

Flower bloom:

*Fragrance*.—Moderate.

*Duration*.—On the plant 4 to 6 days. As a cut flower, 3 to 4 days. Senesced petals drop away cleanly.

*Size*.—Medium for a floribunda. When open, the average flower diameter is 70-80 mm and the average flower height is 60 mm.

*Form*.—Shape of flower when viewed from the side: Upon opening, upper part: Flat. Upon opening, lower part: Flat. Open flower, upper part: Flat. Open flower, lower part: Flattened convex. Overall shape, open flower: Open cup.

Color:

*Upon opening, petals*.—Outermost petals: Outer Side: Orange-White Group 159A. Inner Side: Orange-White Group 159B. Innermost petals: Outer Side: Orange Group 27A. Inner Side: Orange Group 27C at margin with basal zone Yellow-Orange Group 18D.

*Upon opening, basal petal spots*.—Basal petal spot, outermost petals: Outer Side: Yellow Group 13B. Inner Side: Yellow Group 13B. Basal petal spot, innermost petals: Outer Side: Yellow Group 13B. Inner Side: Yellow Group 13B.

*After opening, petals*.—Outermost petals: Outer Side: Red Group 36B. Inner Side: Orange Group 27C. Innermost petals: Outer Side: Orange Group 27A. Inner Side: Orange Group 27C in marginal and middle zone. Basal zone Yellow-Orange Group 18B.

*After opening, basal petal spots*.—Basal petal spot, outermost petals: Outer Side: Yellow Group 7A. Inner Side: Yellow Group 10A. Basal petal spot, innermost petals: Outer Side: Yellow Group 7C. Inner Side Yellow Group 7B.

General tonality: On open flower Orange Group 25D. No change in the general tonality at the end of the 3$^{rd}$ day. Afterwards, general tonality is Orange Group 27B.

Petals:
*Petal count*.—Double (20-40).
*Average range*.—Approximately 23-32 petals under normal conditions.
*Petal reflex*.—Petals reflex somewhat.
*Petal edge*.—Entire to slightly ruffled.
*Petal incisions*.—Absent.
*Petal shape*.—Obovate. Apex shape is obtuse. Shape of base is cuneate.
*Petal size*.—40-45 mm (l) 50-55 mm (w).
*Thickness*.—Average.
*Petal arrangement*.—Not formal.

Petaloids:
*Petaloid count*.—Average of 2-6 per flower.
*Petaloid size*.—Petaloids are 5-15 mm (l) and 3-30 mm (w).
*Petaloid color*.—Color of inner side is Orange Group 27A. Color of outer side is Orange Group 27B.
*Petaloid thickness*.—Thick.
*Petaloid texture*.—Inner Side: Smooth. Outer Side: Smooth.
*Margins*.—Variable, entire to undulated.
*Petaloid shape*.—Spatulate. Apex: Obtuse. Base: Cuneate.

Reproductive organs:
*Pistils*.—Approximately 15-20 present. Stigmas: Location: Slightly inferior in position to anthers. Color: Yellow Group 11B. Styles: Length: About 8 mm long. Color: Greyed-Yellow Group 160C. Intonations of Red Group 46C.
*Stamens*.—Approximately 30 on average and regularly arranged. Anthers: Size: Average 3-4 mm (l)×1 mm (w). Pollen: Generally present. Color: Yellow-Orange Group 22A. Filaments: Color: Yellow Group 12A. Length: 8 mm.

THE PLANT

Growth: Vigorous growth.

Plant habit: Bushy habit. The average plant height is 100 cm and the average plant width is 80 cm.

Stems:
*Stem color*.—Young wood: Yellow-Green Group 146C. Older wood: Yellow-Green Group 146C.
*Stem surface texture*.—Young wood: Smooth. Older wood: Rough.

Prickles: Present.
*Incidence*.—Average of 10 per each 10 cm of stem.
*Size*.—Average length: 8 mm.
*Color*.—Immature prickles: Greyed-Red Group 181A. Mature prickles: Greyed-Orange Group 174A. Senescing to Greyed-Orange Group 165A.
*Shape*.—Concave.

Leaves and leaflets: Normally 7 leaflets on normal leaves in middle of the stem.
*Venation pattern*.—Pyramidal net pattern.
*Leaf size*.—130-170 mm (l)×110-112 mm (w).
*Leaf shape*.—Compound.
*Leaflet arrangement*.—Odd pinnate.
*Leaflet shape*.—Ovate. Base: Obtuse. Apex: Acute.
*Abundance of leaves*.—Average.
*Texture*.—Upper side of leaflet: Leathery. Under side of leaflet: Leathery.
*Leaf surface*.—Semi-glossy.
*Color, mature foliage*.—Upper Leaf Surface: Green Group 137A. Lower Leaf Surface: Yellow-Green Group 147B.
*Color, juvenile foliage*.—Upper Leaf Surface: Yellow-Green Group 146C. Lower Leaf Surface: Yellow-Green Group 146D.
*Anthocyanin intonation*.—Present. Intonations present on juvenile leaf margins, veins, and underside. Greyed-Purple Group 183B.

Stipules:
*Size*.—25 mm long, 12 mm from distal tip to distal tip.
*Stipule color*.—Green Group 137B.
*Anthocyanin*.—Intonations of Greyed-Red Group 181C.
*Stipitate glands*.—Limited. Located along margins.
*Margins*.—Stipitate glands.
*Shape*.—Apex: Apiculate. Base: Flat.

Petiole:
*Length*.—Average 25 mm.
*Diameter*.—Average 3 mm.
*Petiole color*.—Yellow-Green Group 146C.
*Underneath*.—Yellow-Green Group 146B.
*Margins*.—Stipitate glands.
*Anthocyanin*.—Greyed-Red Group 181C on juvenile foliage.
*Prickles*.—Present on underside of mature leaves.
*Stipitate glands*.—Limited number on upper side.

Petiole rachis:
*Length*.—Average 25 mm.
*Diameter*.—Average 25 mm.
*Color*.—Yellow-Green Group 146B. Anthocyanin present on juvenile tissue. Greyed-Red Group 182B.
*Margins*.—Stipitate glands present.
*Prickles*.—A few small prickles underneath on mature foliage.

Leaflets:
*Size*.—Average size of the terminal leaflet is 60-65 mm (l)×40-45 mm (w).
*Shape*.—Entire: Ovate. Base: Obtuse. Apex: Acute.
*Texture*.—Upper side of leaflet: Leathery. Under side of leaflet: Leathery.
*Margins*.—Finely serrated.
*Arrangement*.—Odd pinnate.
*Venation*.—Reticulate.

Hips/seed formation: None observed.

Winter hardiness: To date, the variety has been grown successfully in Zone 5.

Disease resistance: Above average resistance to Powdery mildew (*Sphaerotheca pannosa*), blackspot (*Diplocarpon rosae*), rust (*Phragmidium* sp.), and Botrytis (*Botrytis cinerea*) diseases under normal growing conditions.

I claim:

1. A new and distinct variety of rose plant, as described and illustrated herein.

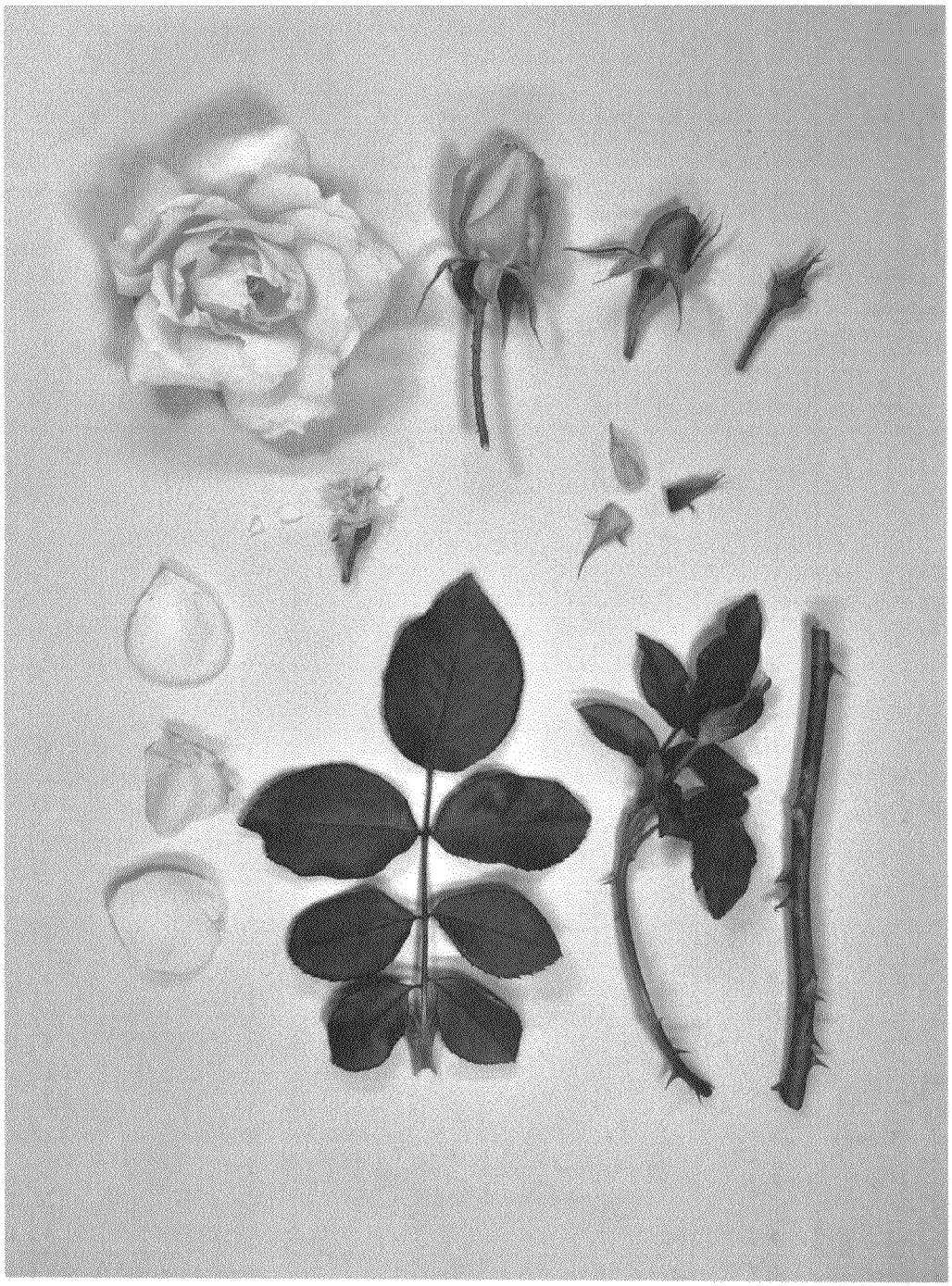

* * * * *